US011970713B2

(12) United States Patent
Tong et al.

(10) Patent No.: US 11,970,713 B2
(45) Date of Patent: Apr. 30, 2024

(54) METHOD FOR LONG-TERM EX VIVO MAINTENANCE OR EXPANSION OF HUMAN ERYTHROBLAST, HUMAN MEGAKARYOCYTE-ERYTHROID PROGENITOR, OR HUMAN COMMON MYELOID PROGENITOR CELL AND APPLICATION THEREOF

(71) Applicant: OCGENE THERAPEUTICS CORPORATION, Monrovia, CA (US)

(72) Inventors: Chang Tong, Glendora, CA (US); Yibin Lin, Irvine, CA (US); Kangtao Lv, Zhengzhou (CN)

(73) Assignee: OCGENE THERAPEUTICS CORPORATION, Monrovia, CA (US)

(*) Notice: Subject to any disclaimer, the term of this patent is extended or adjusted under 35 U.S.C. 154(b) by 167 days.

(21) Appl. No.: 17/540,777

(22) Filed: Dec. 2, 2021

(65) Prior Publication Data
US 2022/0177842 A1  Jun. 9, 2022

Related U.S. Application Data

(60) Provisional application No. 63/121,419, filed on Dec. 4, 2020.

(51) Int. Cl.
*C12N 5/078* (2010.01)
*C12N 15/90* (2006.01)

(52) U.S. Cl.
CPC ......... *C12N 5/0641* (2013.01); *C12N 5/0644* (2013.01); *C12N 15/907* (2013.01); *C12N 2500/25* (2013.01); *C12N 2500/46* (2013.01); *C12N 2501/125* (2013.01); *C12N 2501/14* (2013.01); *C12N 2501/22* (2013.01); *C12N 2501/2303* (2013.01); *C12N 2501/724* (2013.01); *C12N 2501/727* (2013.01)

(58) Field of Classification Search
CPC ... C12N 5/0641; C12N 5/0644; C12N 5/0647
See application file for complete search history.

(56) References Cited

U.S. PATENT DOCUMENTS

2019/0336536 A1* 11/2019 Morrow ............... C12N 5/0647

FOREIGN PATENT DOCUMENTS

WO  WO-2020223517 A1 * 11/2020 ......... A61K 31/4152

OTHER PUBLICATIONS

Flores-Guzman et al. Comparative in vitro analysis of different hematopoietic cell populations from human cord blood: in search of the best option for clinically oriented ex vivo cell expansion. Transfusion 2012, 53:668-678. (Year: 2012).*
Seya et al. Human membrane co-factor protein (MCP, CD46): multiple isoforms and functions. The International Journal of Biochemistry & Cell Biology 1999, 31:1255-1260. (Year: 1999).*
Kim et al. Modulation of β-catenin function maintains mouse epiblast stem cell and human embryonic stem cell self-renewal. Nature Communications 2013, 4:1-11. (Year: 2013).*
Honda et al. Discrimination of stem cell status after subjecting cynomolgus monkey pluripotent stem cells to naive conversion. Scientific Reports 2017, 7:45285. (Year: 2017).*
Li et al. Targeted integration and high-level transgene expression in AAVS1 transgenic mice after in vivo HSC transduction with HDAd5/35++ vectors. Molecular Therapy 2019, 27;12:2195-2212. (Year: 2019).*
Sakurai et al. Efficient gene transfer into human CD34+ cells by an adenovirus type 35 vector. Gene Therapy 2003, 10:1041-1048. (Year: 2003).*
Wong et al. Octanoate in human albumin preparations is detrimental to mesenchymal stromal cell culture. Stem Cells International 2015, 2015:1-9. (Year: 2015).*
Trump et al. Neutrophils derived from genetically modified human induced pluripotent stem cells circulate and phagocytose bacteria in vivo. Stem Cells Translational Medicine 2019, 8:557-567. (Year: 2019).*
Yanagimachi et al. Robust and highly efficient differentiation of functional monocytic cells from human pluripotent stem cells under serum- and feeder cell-free conditions. PLoS One 2013, 8;4:e59243. (Year: 2013).*
Huang et al. Genetically engineered red cells expressing single domain camelid antibodies confer long-term protection against botulinum neurotoxin. Nature Communications 2017, 8;423:1-13. (Year: 2017).*
Kamata et al. A critical function for B-Raf at multiple stages of myelopoiesis. Blood 2005, 106;3:833-840. (Year: 2005).*
International Search Report and Written Opinion issued in corresponding International Application No. PCT/US2021/061779; dated May 13, 2022; 11 pgs.
Tarafdar, Anuradha, et al; Canonical Wnt Signaling Promotes Early Hematopoietic Progenitor Formation and Erythroid Specification during Embryonic Stem Cell Differentiation; PLoS One, Nov. 26, 2013; vol. 8, No. 11; pp. 1-15.
Sheng, Chao, et al; A stably self-renewing adult blood-derived induced neural stem cell exhibiting patternability and epigenetic rejuvenation; Nature Communications, Oct. 2, 2018; vol. 9, No. 4047; pp. 1-15.
Richter, Maximilian, et al; In vivo transduction of primitive mobilized hematopoietic stem cells after intravenous injection of integrating adenovirus vectors; Blood, Nov. 3, 2016; vol. 128, No. 18, pp. 2206-2217.

* cited by examiner

*Primary Examiner* — Allison M Fox
*Assistant Examiner* — Jennifer S Spence
(74) *Attorney, Agent, or Firm* — HAUPTMAN HAM, LLP (57) ABSTRACT

The invention relates to a method for long-term ex vivo maintenance or expansion of one or more of a human erythroblast, a human megakaryocyte-erythroid progenitor, or a human common myeloid progenitor, comprising the step of: culturing cells comprising one or more of those cells in a culture medium comprising one or more selected from a tankyrase inhibitor, a growth factor, a B-Raf kinase inhibitor and a GSK-3 inhibitor.

15 Claims, 8 Drawing Sheets

METHOD FOR LONG-TERM EX VIVO MAINTENANCE OR EXPANSION OF HUMAN ERYTHROBLAST, HUMAN MEGAKARYOCYTE-ERYTHROID PROGENITOR, OR HUMAN COMMON MYELOID PROGENITOR CELL AND APPLICATION THEREOF

CROSS-REFERENCE TO RELATED APPLICATIONS

This patent application claims benefit of U.S. Provisional Patent Application Ser. No. 63/121,419 filed Dec. 4, 2020, which is incorporated herein by reference.

TECHNICAL FIELD

The disclosure provides method for long-term ex vivo maintenance or expansion of human erythroblast, human megakaryocyte-erythroid progenitor, and human common myeloid progenitor cell and application thereof.

BACKGROUND

The human hematopoietic system comprises adaptive immune cells, innate immune cells, megakaryocytes, and erythrocytes. All of these cell types originate from human hematopoietic stem cells (hHSCs), which differentiate into common lymphoid progenitor cells and common myeloid progenitor (hCMP) cells. The common lymphoid progenitor cells further develop into adaptive immune cells, including B lymphocytes and T lymphocytes; and, the common myeloid progenitor cells mature into either megakaryocyte-erythrocyte progenitor (hMEP) or granulocyte-monocyte progenitor (hGMP) cells. Furthermore, the megakaryocyte-erythrocyte progenitor can further differentiate into megakaryocytes and erythroblasts that finally mature into platelets and erythrocytes. The granulocyte-monocyte progenitor cells, on the other hand, mature into the innate immune cells, including monocytes, basophils, eosinophils, and neutrophils. Monocytes finally differentiate into macrophages and dendritic cells.

Different cells play different roles in clinical practice, however, the lack of a method for massive expansion and long-term maintenance of human cells ex vivo hinders clinical application. Several methods for the expansion of myeloid-originated cells or progenitors thereof have been reported, most of which used many different combinations of growth factors. However, only limited capacity to expand cells from human was achieved in those methods.

SUMMARY

Provided herein is a method for long-term ex vivo maintenance or expansion of human erythroblast, human megakaryocyte-erythroid progenitor, and human common myeloid progenitor cell and an application thereof.

The disclosure provides a method for long-term ex vivo maintenance or expansion of one or more of a human erythroblast, a human megakaryocyte-erythroid progenitor, or a human common myeloid progenitor, comprising the step of:

culturing the cells comprising one or more of the human erythroblast, the human megakaryocyte-erythroid progenitor, or the human common myeloid progenitor in a culture medium, wherein the culture medium comprises one or more selected from a tankyrase inhibitor, a growth factor, a B-Raf kinase inhibitor and a GSK-3 inhibitor.

In at least one embodiment, the tankyrase inhibitor is one or more of XAV939, AZ-6102, JW-55, MN-64, TC-E 5001, WIKI4, RK-287107, MSC2504877, or G007-LK.

In at least one embodiment, the tankyrase inhibitor is XAV939.

In at least one embodiment, the concentration of the tankyrase inhibitor in the culture medium is from 0.1 µM to 900 µM.

In at least one embodiment, the B-Raf kinase inhibitor is one or more of GDC-0879, PLX4032, L-779450, GSK2118436, L-779450, DABRAFENIB, RAF709, BMS-908662, LGX818, PLX3603, RAF265, RO5185426, vemurafenib, PLX8394, or SB590885.

In at least one embodiment, the B-Raf kinase inhibitor is SB590885.

In at least one embodiment, the GSK-3 inhibitor is one or more of CHIR99021, CHIR98014, LY2090314, ALSTER-PAULLONE, BIO-ACETOXIME, AZD1080, 2-D08, SB216763, BIO, SB415286, TWS119, Tideglusib, A1070722, or AR-A014418; alternatively the GSK-3 inhibitor is CHIR99021.

In at least one embodiment, the growth factor is a stem cell factor (SCF).

In at least one embodiment, the concentration of the B-Raf kinase inhibitor in the culture medium is from 0.1 µM to 70 µM, the concentration of the tankyrase inhibitor in the culture medium is from 0.1 µM to 900 µM, the concentration of the GSK-3 inhibitor in the culture medium is from 0.1 µM to 70 µM, and the concentration of the stem cell factor in the culture medium is from 10 ng/ml to 100 ng/ml.

In at least one embodiment, a basal medium of the culture medium comprises one or more of DMEM/F12, IMDM, and Neural Basal Medium.

In at least one embodiment, the DMEM/F12 and the Neural Basal Medium in the culture medium are in a ratio of 5:1 to 1:5.

In at least one embodiment, the IMDM and the Neural Basal Medium in the culture medium are in a ratio of 5:1 to 1:5.

In at least one embodiment, the ratio of 1:1 for the DMEM/F12 and the Neural Basal Medium is used in the culture medium.

In at least one embodiment, the tankyrase inhibitor is XAV939, the B-Raf kinase inhibitor is SB590885, the GSK-3 inhibitor is CHIR99021, and the growth factor is stem cell factor.

In at least one embodiment, the concentration of XAV939 in the culture medium is 0.1 µM-20 µM; the concentration of SB590885 in the culture medium is not more than 5 µM, optionally 0.1 µM-5 µM; the concentration of CHIR99021 in the culture medium is not more than 10 µM, optionally 0.1 µM-10 µM; and the concentration of the stem cell factor in the culture medium is from 10 ng/ml to 100 ng/ml.

In at least one embodiment, the culture medium further comprises one or more supplements of insulin, transferrin, HSA, putrescine, progesterone, or linolenic acid.

In at least one embodiment, the culture medium is supplemented with insulin, transferrin, HSA, putrescine, progesterone, and linolenic acid.

In at least one embodiment, the human erythroblast, the human megakaryocyte-erythroid progenitor, or the human common myeloid progenitor cell is derived from a stem cell; alternatively, from a hematopoietic stem cell; and, further alternatively, the hematopoietic stem cell is in a form of a human umbilical cord blood mononuclear cell.

In at least one embodiment, any of the human erythroblast, the human megakaryocyte-erythroid progenitor, or the human common myeloid progenitor is capable to expand long term in the ex vivo culture medium, the obtained cells after expansion remain morphologically unchanged and have the capacity to differentiate and the obtained cells after expansion are $CD46^+$.

The disclosure also provides a method to genetically modify one or more of a human erythroblast, a human megakaryocyte-erythroid progenitor, or a human common myeloid progenitor obtained by the method of claim 1, comprising the step of:

performing a genetic engineering modification to one or more of the human erythroblast, the human megakaryocyte-erythroid progenitor, or the human common myeloid progenitor expanded by the method of claim 1, using a gene editing system, a homologous recombination, or a site directed mutagenesis; alternatively, the gene editing system is a TALEN- or CRISPR-based system.

In at least one embodiment, the genetic engineering modification comprises replacing or disrupting an existing gene (knockout), or altering a genetic locus to contain sequence information not found at the genetic locus (knock-in).

In at least one embodiment, the genetic engineering modification is operated with Ad35 adenovirus.

The disclosure also provides a method for differentiation of one or more of a human erythroblast, a human megakaryocyte-erythroid progenitor, or a human common myeloid progenitor expanded by the method of claim 1, comprising the step of: culturing the human erythroblast, the human megakaryocyte-erythroid progenitor, and the human common myeloid progenitor cell with a differentiation medium.

In at least one embodiment, the differentiation medium is a neutrophil differentiation medium comprising one or more of RPMI 1640 culture medium, DMEM media, 10% FBS, and 20 ng/mL of GCSF.

In at least one embodiment, the differentiation medium is a monocyte differentiation medium comprises one or more of RPMI 1640 culture medium, DMEM media, 10% FBS, and 20 ng/mL of GM-CSF.

In at least one embodiment, the differentiation medium is a red blood cells differentiation medium comprises one or more of IMDM, insulin, holo-transferrin, IL-3, EPO, and SCF.

The disclosure also provides a culture medium for long-term ex vivo maintenance or expansion of one or more of a human erythroblast, a human megakaryocyte-erythroid progenitor, or a human common myeloid progenitor, comprising one or more selected from a tankyrase inhibitor, a growth factor, a B-Raf kinase inhibitor and a GSK-3 inhibitor.

In at least one embodiment, the tankyrase inhibitor is one or more of XAV939, AZ-6102, JW-55, MN-64, TC-E 5001, WIKI4, RK-287107, MSC2504877, or G007-LK.

In at least one embodiment, the tankyrase inhibitor is XAV939.

In at least one embodiment, the concentration of the tankyrase inhibitor in the culture medium is from 0.1 µM to 900 µM.

In at least one embodiment, the B-Raf kinase inhibitor is one or more of GDC-0879, PLX4032, GSK2118436, L-779450, DABRAFENIB, RAF709, BMS-908662, LGX818, PLX3603, RAF265, R05185426, vemurafenib, PLX8394, or SB590885.

In at least one embodiment, the B-Raf kinase inhibitor is SB590885.

In at least one embodiment, the GSK-3 inhibitor is one or more of CHIR99021, CHIR98014, LY2090314, ALSTER-PAULLONE, BIO-ACETOXIME, AZD1080, 2-D08, SB216763, BIO, SB415286, TWS119, Tideglusib, A1070722, or AR-A014418.

In at least one embodiment, the GSK-3 inhibitor is CHIR99021.

In at least one embodiment, the growth factor is a stem cell factor (SCF).

In at least one embodiment, the concentration of the B-Raf kinase inhibitor in the culture medium is from 0.1 µM to 70 µM, the concentration of the tankyrase inhibitor in the culture medium is from 0.1 µM to 900 µM, the concentration of the GSK-3 inhibitor in the culture medium is from 0.1 µM to 70 µM, and the concentration of the stem cell factor in the culture medium is from 10 ng/ml to 100 ng/ml.

In at least one embodiment, the basal medium of the culture medium comprises DMEM/F12, IMDM, and Neural Basal Medium.

In at least one embodiment, the DMEM/F12 and the Neural Basal Medium in the culture medium are in a ratio of 5:1 to 1:5, alternatively in a ratio of 1:1.

In at least one embodiment, the IMDM and the Neural Basal Medium in the culture medium are in a ratio of 5:1 to 1:5, alternatively in a ratio of 1:1.

In at least one embodiment, the tankyrase inhibitor is XAV939, the B-Raf kinase inhibitor is SB590885, the GSK-3 inhibitor is CHIR99021, and, the growth factor is stem cell factor.

In at least one embodiment, the concentration of XAV939 in the culture medium is 0.1 µM-20 µM; the concentration of SB590885 in the culture medium is not more than 5 µM, optionally 0.1 µM-5 µM; the concentration of CHIR99021 in the culture medium is not more than 10 µM, optionally 0.1 µM-10 µM; and the concentration of the stem cell factor in the culture medium is from 10 ng/ml to 100 ng/ml.

In at least one embodiment, the culture medium further comprises one or more supplements of insulin, transferrin, HSA, putrescine, progesterone, and linolenic acid.

In at least one embodiment, the culture medium is supplemented with insulin, transferrin, HSA, putrescine, progesterone, and linolenic acid.

In at least one embodiment, the human erythroblast, the human megakaryocyte-erythroid progenitor, or the human common myeloid progenitor cell is derived from an umbilical cord blood mononuclear cell, a hematopoietic stem cell, an embryonic stem cell, an induced pluripotent stem cell or a non-embryonic (adult) stem cell.

In at least one embodiment, any of the human erythroblast, the human megakaryocyte-erythroid progenitor, or the human common myeloid progenitor can expand long term in the ex vivo culture medium, and the obtained cells after expansion remain morphologically unchanged and have the capacity to differentiate.

The human erythroblast, human megakaryocyte-erythroid progenitor, and human common myeloid progenitor generated by the long-term ex vivo expansion of the disclosure, can be readily differentiated to macrophages, neutrophils, basophils, dendritic cells, platelets, and red blood cells. In addition, it is also susceptible to genetic modification techniques, thereby allowing for a genetic use of the human erythroblast, human megakaryocyte-erythroid progenitor, and human common myeloid progenitor cell in basic scientific research and clinical therapeutic application. The genetically modified macrophages derivate from genetically modified human common myeloid progenitor cells are expected to have enhanced antitumor effects and can be used clinically to treat cancer, either as monotherapy or combination therapy with other immunological agents, such as anti-PD-1/PD-L1 antibodies and chimeric antigen receptor T (CAR-T) cells. Furthermore, the genetically modified red blood cells derivate from genetically modified human erythroblasts are expected to also have antivirus effects and antitumor effects, and can be used clinically to treat different types of cancer.

The tankyrase inhibitor or the tankyrase in combination of a growth factor, a B-Raf kinase inhibitor and a GSK-3 inhibitor has a great potential in expanding the human erythroblast, the human megakaryocyte-erythroid progenitor, and the human common myeloid progenitor cells from cord blood cells. The whole nucleated cells in human cord blood can be expanded 50 to 10000 folds in about three weeks, and the cells can be maintained in this medium to 18 passages or more.

DETAILED DESCRIPTION

As used herein and in the appended claims, the singular forms "a," "an," and "the" include plural referents unless the context clearly dictates otherwise. Thus, for example, reference to "a cell" includes a plurality of cells and reference to "a human erythroblast, a human megakaryocyte-erythroid progenitor, and a human common myeloid progenitor cell" includes reference to one or more of the human erythroblasts, human megakaryocyte-erythroid progenitors, and human common myeloid progenitor cells and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of".

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

One of ordinary skill in the art would understand that this disclosure is not limited to the particular methodology, protocols, and reagents, etc., described herein and as such may vary. The terminology used herein is for the purpose of describing particular embodiments only and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used to described the present disclosure, in connection with percentages means±10%.

The inhibition of two protein kinases, the mitogen-activated protein kinase (MEK) and glycogen synthase kinase 3 (GSK3), allows long-term self-renewal of mouse and rat embryonic stem cells (ESCs). Based on this finding, the inventors postulated that many, if not all, types of stem cells can be maintained during long-term ex vivo culture by inhibiting signaling pathways responsible for initiating differentiation. As known by the inventors, the selection of different inhibitors is important, and some of the pathway inhibitors may cause the death of certain kinds of cells. In our previous work, a medium named 3i (The basal medium supplemented with 3i composition, namely SCF+ SB590885+CHIR99021) for expanding granulocyte-monocyte progenitor cells was developed, with which mouse GMP cells can be expanded effectively; however, only limited capacity in expanding cells from human was achieved. After further chemical screening using human umbilical cord blood mononuclear cell, a tankyrase inhibitor, that may function by targeting Wnt/β-catenin signaling, was found to promote the expansion of a human erythroblast, a human megakaryocyte-erythroid progenitor, or a human common myeloid progenitor; alternatively promote the expansion of human erythroblast. The tankyrase inhibitor in combination with a growth factor, a B-Raf kinase inhibitor and a GSK3 inhibitor allowed for the production of a uniform cell population of bright, small and round-shaped cells which could further undergo long term cell expansion.

The disclosure provides methods for long-term ex vivo maintenance or expansion of one or more of a human erythroblast, a human megakaryocyte-erythroid progenitor, or a human common myeloid progenitor, comprising the step of: culturing the cell comprising one or more cell of human erythroblast, the human megakaryocyte-erythroid progenitor, or the human common myeloid progenitor in a culture medium comprising one or more selected from a tankyrase inhibitor, a growth factor, a B-Raf kinase inhibitor, and a GSK-3 inhibitor.

The disclosure also provides cultures medium for long-term ex vivo maintenance or expansion of one or more of a human erythroblast, a human megakaryocyte-erythroid progenitor, or a human common myeloid progenitor, comprising one or more selected from a tankyrase inhibitor, a growth factor, a B-Raf kinase inhibitor, and a GSK-3 inhibitor.

In at least one embodiment, the tankyrase inhibitor is one or more of XAV939, AZ-6102, JW-55, MN-64, TC-E 5001, WIKI4, RK-287107, MSC2504877, or G007-LK.

In at least one embodiment, the tankyrase inhibitor is XAV939.

In at least one embodiment, the concentration of the tankyrase inhibitor in the culture medium is from 0.1 µM to 900 µM.

In at least one embodiment, the B-Raf kinase inhibitor is one or more of GDC-0879, PLX4032, GSK2118436, L-779450, DABRAFENIB, RAF709, BMS-908662, LGX818, PLX3603, RAF265, R05185426, vemurafenib, PLX8394, or SB590885; alternatively the B-Raf kinase inhibitor is SB590885.

In a further embodiment, the GSK-3 inhibitor is one or more of CHIR99021, CHIR98014, LY2090314, ALSTERPAULLONE, BIO-ACETOXIME, AZD1080, 2-D08, SB216763, BIO, SB415286, TWS119, Tideglusib, A1070722, or AR-A014418.

In at least one embodiment, the GSK-3 inhibitor is CHIR99021.

In at least one embodiment, the growth factor is a stem cell factor (SCF).

In at least one embodiment, the concentration of the B-Raf kinase inhibitor in the culture medium is from 0.1 µM to 70 µM, the concentration of the tankyrase inhibitor in the culture medium is from 0.1 µM to 900 µM, the concentration of the GSK-3 inhibitor in the culture medium is from 0.1 µM to 70 µM, and the concentration of the stem cell factor in the culture medium is from 10 ng/ml to 100 ng/ml.

In at least one embodiment, the basal medium of the culture medium comprises DMEM/F12 and Neural Basal Medium. The basal medium refers to a solution of amino acids, vitamins, salts, and nutrients that is effective to support the growth of cells in culture. The nutrients include a carbon source (e.g., a sugar such as glucose) that can be metabolized by the cells, as well as other compounds necessary for the cell's survival. These are compounds that the cells themselves cannot synthesize, due to the absence of one or more of the gene(s) that encode the protein(s) necessary to synthesize the compound (e.g., essential amino acids), or compounds which the cells can synthesize, while the gene(s) encoding the necessary biosynthetic proteins are not being expressed as sufficient levels because of their particular developmental state. A number of basal medium are known in the art of mammalian cell culture, such as Dulbecco's Modified Eagle Media (DMEM), Iscove's Modified Dulbecco's Medium (IMDM), RPMI 1640, Knockout-DMEM (KO-DMEM), DMEM/F12, and Neural Basal Medium. Alternatively, a culture medium that comprises DMEM/F12 and a Neural Basal Medium with a ratio of 5:1 to 1:5 can be used to culture the human erythroblast, the human megakaryocyte-erythroid progenitor, or the human common myeloid progenitor.

In at least one embodiment, the tankyrase inhibitor is XAV939, the B-Raf kinase inhibitor is SB590885, the GSK-3 inhibitor is CHIR99021, and, the growth factor is stem cell factor. The human erythroblast, the human megakaryocyte-erythroid progenitor, or the human common myeloid progenitor can grow and expand in a culture medium which includes a combination of factors and agents including, but not limited to, a growth factor (e.g., SCF), a tankyrase inhibitor (e.g., XAV939), a B-Raf kinase inhibitor (e.g., SB590885), and a GSK-3 inhibitor (e.g., CHIR99021).

In at least one embodiment, the concentration of XAV939 in the culture medium is 0.1 µM-20 µM; the concentration of SB590885 in the culture medium is not more than 5 µM, 0.1 µM-5 µM; the concentration of CHIR99021 in the culture medium is not more than 10 µM, 0.1 µM-10 µM; and the concentration of the stem cell factor in the culture medium is from 10 ng/ml to 100 ng/ml.

In at least one embodiment, the culture medium could be supplemented with one or more additional agents, including, but not limited to insulin, transferrin, HSA, putrescine, progesterone, linolenic acid. The basal medium is supplemented with various other biological agents that support the growth of stem cells in a substantially undifferentiated state.

In at least one embodiment, the human erythroblast, the human megakaryocyte-erythroid progenitor, or the human common myeloid progenitor cell was derived from an umbilical cord blood mononuclear cell, a hematopoietic stem cell, an embryonic stem cell, an induced pluripotent stem cell or a non-embryonic (adult) stem cell. A stem cell is a cell capable of differentiation into other cell types, including those having a particular, specialized function (e.g., tissue specific cells, parenchymal cells and progenitors thereof). Progenitor cells (i.e., "multipotent") are cells that can give rise to different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming these stem cells are unable to de-differentiate into the cells from which they were derived. As will be appreciated, "multipotent" stem/progenitor cells (e.g., human common myeloid progenitor (hCMPs)) have a narrower differentiation potential than do pluripotent stem cells. Prior to derivation into hCMPs, the stem cells disclosed herein can be genetically modified by use of any number of genetic engineering techniques, e.g., such as gene therapy, gene editing systems, homologous recombination, etc. Such modified stem cells may provide for enhanced therapies (e.g., see Nowakowski et al., *Acta Neurobiol Exp (Wars)* 73(1):1-18 (2013)).

In at least one embodiment, the human erythroblast, the human megakaryocyte-erythroid progenitor, or the human common myeloid progenitor cell of the disclosure is derived from umbilical cord blood mononuclear cells. Umbilical cord blood is the blood left over in the placenta and in the umbilical cord after the birth of the baby. The umbilical cord blood is composed of all the elements found in whole blood. The umbilical cord blood contains red blood cells, white blood cells, plasma, platelets and is also rich in hematopoietic stem cells. Hematopoietic stem cells can be isolated from cord blood using any number of isolation methods taught in the art, including those taught in Chularojmontri et al., *J Med Assoc Thai* 92(3): S88-94 (2009). Moreover, commercial kits are available for isolation $CD34^+$ cells (i.e., hematopoietic stem cells) from human umbilical cord blood from multiple vendors, including STEMCELL Technologies, Thermo Fisher Scientific, Zen-Bio, etc.

In at least one embodiment, the human erythroblast, the human megakaryocyte-erythroid progenitor, or the human common myeloid progenitor cell of the disclosure is derived from hematopoietic stem cells (HSCs). HSCs can easily be isolated from umbilical cord blood and bone marrow. Such isolation protocols are known in the art and typically use $CD34^+$ as a cell selection marker for the isolation of HSCs (e.g., see Lagasse et al., *Nat Med.* 6:1229-1234 (2000)).

In at least one embodiment, the human erythroblast, the human megakaryocyte-erythroid progenitor, or the human common myeloid progenitor cell of the disclosure is derived from embryonic stem cells (ESCs). ESCs are stem cells derived from the undifferentiated inner mass cells of a human embryo. Embryonic stem cells are pluripotent, meaning they are able to grow (i.e. differentiate) into all derivatives of the three primary germ layers: ectoderm, endoderm and mesoderm. Additionally, under defined conditions, embryonic stem cells are capable of propagating themselves indefinitely.

In at least one embodiment, the human erythroblast, the human megakaryocyte-erythroid progenitor, or the human common myeloid progenitor cell of the disclosure is derived from the induced pluripotent stem cell (iPSs, or iPSCs). iPSCs are a type of pluripotent stem cell obtained from non-pluripotent cells by selective gene expression (of endogenous genes) or by transfection with a heterologous gene. Induced pluripotent stem cells are described by Shinya Yamanaka's team at Kyoto University, Japan. Yamanaka had identified genes that are particularly active in embryonic stem cells and used retroviruses to transfect mouse fibroblasts with a selection of those genes. Eventually, four key pluripotency genes essential for the production of pluripotent stem cells were isolated; Oct-3/4, SOX2, c-Myc, and Klf4. Cells were isolated by antibiotic selection for $Fbx15^+$ cells. The same group published a study along with two other independent research groups from Harvard, MIT, and the University of California, Los Angeles, showing successful reprogramming of mouse fibroblasts into iPS and even producing a viable chimera.

In at least one embodiment, the human erythroblast, the human megakaryocyte-erythroid progenitor, or the human common myeloid progenitor cell of the disclosure is derived from non-embryonic (adult) stem cells. The non-embryonic stem cell can renew itself and can differentiate to yield some or all of the major specialized cell types of the tissue or organ. The primary roles of non-embryonic stem cells in a living organism are to maintain and repair the tissue in which they are found. Scientists also use the term somatic stem cell instead of non-embryonic stem cell, where somatic refers to cells of the body (not the germ cells, sperm or eggs). Non-embryonic stem cells have been identified in many organs and tissues, including brain, bone marrow, peripheral blood, blood vessels, skeletal muscle, skin, teeth, heart, gut, liver, ovarian epithelium, and testis. Non-embryonic stem cells are thought to reside in a specific area of each tissue (called a "stem cell niche"). In a living animal, non-embryonic stem cells are available to divide for a long period, when needed, and can give rise to mature cell types that have characteristic shapes and specialized structures and functions of a particular tissue. Pluripotency distinguishes embryonic stem cells from non-embryonic stem cells found in adults; embryonic stem cells can generate all cell types in the body, while adult stem cells are multipotent and can produce only a limited number of cell types.

In at least one embodiment, any of the human erythroblast, the human megakaryocyte-erythroid progenitor, or the human common myeloid progenitor is capable to expand long term in the ex vivo culture medium, the obtained cells after expansion remain morphologically unchanged and have the capacity to differentiate and the obtained cells after expansion are $CD46^+$. A 4-, 10-, 20-, 50-, 100-, 1000-, or more fold expanded population of the human erythroblast, the human megakaryocyte-erythroid progenitor, and the human common myeloid progenitor can be obtained, compared to the previous starting cell population. The degree of expansion per passage can be calculated by dividing the approximate number of cells harvested at the end of the culture by the approximate number of cells originally seeded into the culture. When geometry of the growth environment is limiting or for other reasons, the cells may optionally be passaged into a similar growth environment for further expansion. The total expansion is the product of all the expansions in each of the passages. Of course, retaining all the expanded cells on each passage is not necessary. For example, if the cells expand two-fold in each culture, but only about 50% of the cells are retained on each passage, then approximately the same number of cells will be carried forward. But after four cultures, the cells are said to have undergone an expansion of 16-fold. Cells may be stored by cryogenic freezing techniques known in the art. Under suitable conditions, cells in the expanded population will be 50%, 70%, or more in the undifferentiated state.

The disclosure also provides a method to genetically modify one or more of the human erythroblast, the human megakaryocyte-erythroid progenitor, or the human common myeloid progenitor expanded by the above method, comprising the step of: a genetic engineering modification into one or more of the human erythroblast, the human megakaryocyte-erythroid progenitor, or the human common myeloid progenitor expanded by the above method, using a gene editing system, homologous recombination, or site directed mutagenesis; alternatively, the gene editing system is a TALEN- or CRISPR-based system. Another alternated example of gene modification is using viral vectors or non-viral vectors. As shown herein, the cells of the disclosure are susceptible to genetic modification techniques, thereby allowing for the use of the human erythroblast, human megakaryocyte-erythroid progenitor, and human common myeloid progenitor cells in basic scientific research and clinical therapeutic applications. Thus, expanded and genetically modified human erythroblast, human megakaryocyte-erythroid progenitor, and human common myeloid progenitor can be readily applied in broad clinical applications.

In at least one embodiment, the genetically engineering modification comprises replacing or disrupting an existing gene (knockout), or altering a genetic locus to contain sequence information not found at the genetic locus (knock-in).

In at least one embodiment, the genetically engineering modification is operated with Ad35 adenovirus.

The disclosure further provides a method for differentiation of one or more of the human erythroblast, the human megakaryocyte-erythroid progenitor, or the human common myeloid progenitor expanded by the method of claim 1, comprising the step of: culturing the human erythroblast, human megakaryocyte-erythroid progenitor, and human common myeloid progenitor cells with a differentiation medium. The human erythroblast, human megakaryocyte-erythroid progenitor, or human common myeloid progenitor is differentiated into myeloid lineages of blood cells, such as monocytes, macrophages, granulocytes, neutrophils, basophils, eosinophils, erythrocytes, megakaryocytes to platelets and dendritic cell.

In at least one embodiment, a method disclosed herein further comprises differentiating the human erythroblast, human megakaryocyte-erythroid progenitor, or human common myeloid progenitor cells of the disclosure into neutrophil and monocytes by culturing the cells with a neutrophil differentiation medium comprising one or more of RPMI1640, DMEM, 10% FBS and G-CSF.

In at least one embodiment, the macrophage differentiation medium comprises one or more of RPMI 1640, DMEM, 10% FBS and GM-CSF.

As will be appreciated, replacing spent culture medium with fresh culture medium either continually, or at periodic intervals, typically every 1 to 3 days is beneficial. One advantage of using fresh medium is the ability to adjust conditions so that the cells expand more uniformly and rapidly than when cultured on feeder cells, according to some techniques, or in conditioned medium.

A "growth factor" refers to a substance that is effective to promote the growth of stem cells and which, unless added to the culture medium as a supplement, is not otherwise a component of the basal medium. Growth factors include, but are not limited to, stem cell factor (SCF), basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, Wnt and bone morphogenic proteins (BMPs), cytokines, chemokines, morphogens, neutralizing antibodies, other proteins, and small molecules. Exogenous growth factors may also be added to a medium according to the disclosure to assist in the maintenance of cultures of the human erythroblast, the human megakaryocyte-erythroid progenitor, or the human common myeloid progenitor in a substantially undifferentiated state. Such factors and their effective concentrations can be identified as described elsewhere herein or using techniques known to those of skill in the art of culturing cells. In at least one embodiment, the human erythroblast, the human megakaryocyte-erythroid progenitor, or the human common myeloid progenitor are cultured in a culture medium which comprises human SCF as a growth factor.

A "B-Raf kinase inhibitor" refers to a substance that blocks a protein called B-Raf. B-Raf is a kinase that helps control cell growth and signaling. It may be found in a mutated (changed) form in some types of cancer, including melanoma and colorectal cancer. Some B-Raf kinase inhibitors are used to treat cancer. Examples of B-Raf kinase inhibitor includes, but are not limited to, GDC-0879, PLX4032, GSK2118436, L-779450, DABRAFENIB, RAF709, BMS-908662, LGX818, PLX3603, RAF265, R05185426, vemurafenib, PLX8394, and SB590885. In a particular embodiment, a method disclosed herein comprises use of the B-Raf kinase inhibitor SB590885.

A "tankyrase inhibitor" refers to a substance that blocks a protein called tankyrase. Tankyrase, also known as tankyrase 1, is an enzyme that in humans is encoded by the TNKS gene. It inhibits the binding of TERF1 to telomeric DNA. Tankyrase acts as an activator of the Wnt signaling pathway by mediating poly-ADP-ribosylation (PARylation) of AXIN1 and AXIN2, 2 key components of the beta-catenin destruction complex. Poly-ADP-ribosylated target proteins are recognized by RNF146, which mediates their ubiquitination and subsequent degradation. Tankyrase also mediates PARsylation of BLZF1 and CASC3, followed by recruitment of RNF146 and subsequent ubiquitination. Tankyrase mediates PARsylation of TERF1, thereby contributing to the regulation of telomere length. Tankyrase is involved in centrosome maturation during prometaphase by mediating PARsylation of HEPACAM2/MIKI. May also regulate vesicle trafficking and modulate the subcellular distribution of SLC2A4/GLUT4-vesicles. Tankyrase may be involved in spindle pole assembly through PARsylation of NUMA1. Stimulates 26S proteasome activity. While any function mechanism of the tankyrase inhibitors is not a limitation of this disclosure. Examples of tankyrase inhibitor include, but are not limited to, XAV939, AZ-6102, JW-55, MN-64, TC-E 5001, WIKI4, RK-287107, MSC2504877, and G007-LK. In a particular embodiment, a method disclosed herein comprises use of the tankyrase inhibitor XAV939.

A "GSK-3 inhibitor" as used herein refers to a compound or small molecule that inhibits the action of glycogen synthase kinase 3. Glycogen synthase kinase 3 is a serine/threonine protein kinase that mediates the addition of phosphate molecules onto serine and threonine amino acid residues. In mammals GSK-3 is encoded by two known genes, GSK-3 alpha (GSK3A) and GSK-3 beta (GSK3B). GSK-3 has recently been the subject of much research because it has been implicated in a number of diseases, including Type II diabetes (Diabetes mellitus type 2), Alzheimer's Disease, inflammation, cancer, and bipolar disorder. GSK-3 is active in a number of central intracellular signaling pathways, including cellular proliferation, migration, glucose regulation, and apoptosis. GSK-3 has also been shown to regulate immune and migratory processes. GSK-3 participates in a number of signaling pathways in the innate immune response, including pro-inflammatory cytokine and interleukin production. GSK-3 is also integrally tied to pathways of cell proliferation and apoptosis. GSK-3 has been shown to phosphorylate Beta-catenin, thus targeting it for degradation. Examples of GSK-3 inhibitors include, but are not limited to, CHIR99021, CHIR98014, LY2090314, ALSTERPAULLONE, BIO-ACETOXIME, AZD1080, 2-D08, SB216763, BIO, A1070722, and AR-A014418. In a particular embodiment, a method disclosed herein comprises use of the GSK inhibitor CHIR99021.

The expression of "long-term ex vivo maintenance or expansion" presents an ex vivo maintenance or expansion longer than 2 weeks, such as: 3, 4, 5, 6, 7, 8, 9, 10 weeks or even longer.

The following examples are intended to illustrate, but not limit the disclosure. While the following examples are types of examples that might be used, other procedures known to those skilled in the art may alternatively be used.

The materials used in the examples are commercially available

Example 1. 3i+X Composition Promotes a Cell Expansion

To determine whether the tankyrase is important for the long-term expansion of the human erythroblast, the human megakaryocyte-erythroid progenitor, or the human common myeloid progenitor, $1\times10^7$ of human umbilical cord blood mononuclear cells were seeded in E6 medium supplemented with 3i+X composition (5 μM of Chir99021+0.5 μM of SB590885+50 ng/ml of SCF+0.5 μM of XAV939) as a experimental group, or seeded in E6 medium as a blank group, or seeded in E6 medium supplemented with 3i composition (5 μM of Chir99021+2 μM of SB590885+50 ng/ml of SCF) only as a control group. The basal medium of DMEM/F12 and Neural Basal Medium (mixed in 1:1 ratio) supplemented with insulin, transferrin, HSA, putrescine, progesterone, and linolenic acid was referred as E6 medium in the disclosure.

Figure 1:
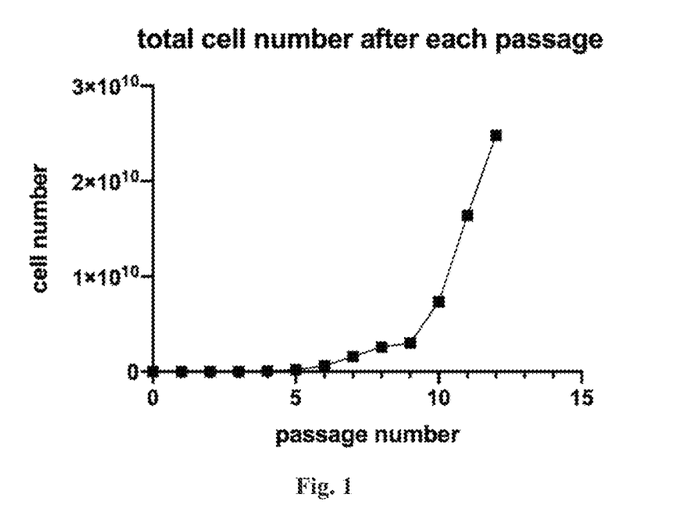
FIG. 1 is a graph of the total cell number after each cell passage in the long-term culture of human umbilical cord blood mononuclear cells in the experimental group. $1 \times 10^7$ of human umbilical cord blood mononuclear cells were seeded, and $2.48 \times 10^{10}$ cells can be achieved at passage $12^{th}$.
Figure 2:
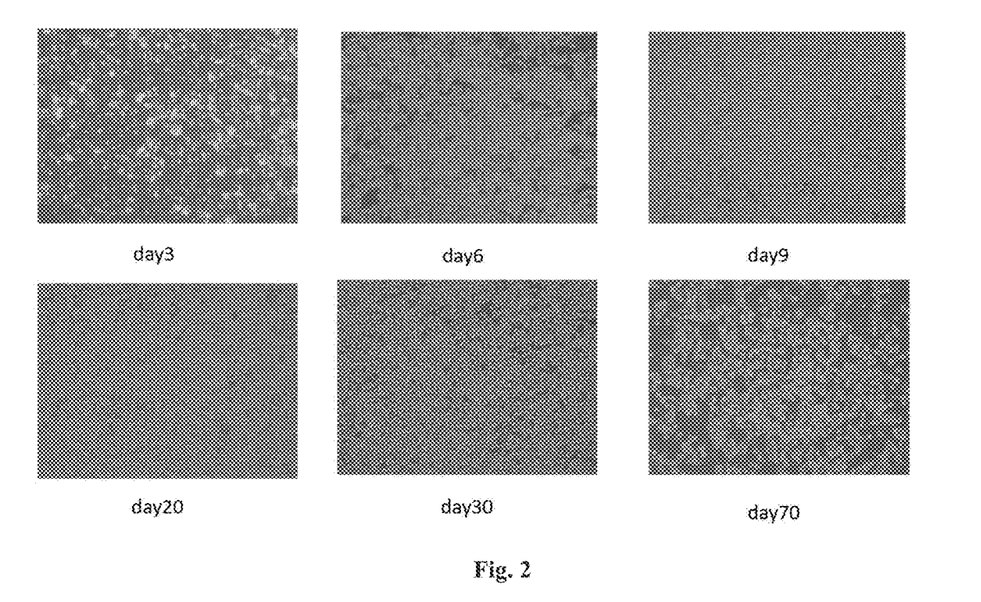
FIG. 2 is bright field images of regular invert microscope of cells at different time point in the long-term culture of human umbilical cord blood mononuclear cells in the experimental group. The obtained cells remained morphologically unchanged.

Results: After 20 days (passage $7^{th}$), almost half of cells died in the control group. In contrast, cells of the experimental group could be propagated for more than 60 days, and $2.48\times10^{10}$ cells can be achieved at passage $12^{th}$ (showed in FIG. 1 and Table 1). The obtained cells remained morphologically unchanged (showed in FIG. 2). As for the blank group that none of 3i+X composition was contained in the culture medium, the cell number dramatically decreased with the passage of time, from $1.19\times10^6$ cells/ml at Day 0, to $1.90\times10^5$ cells/ml at passage 1, and until to $2.30\times10^4$ cells/ml at passage 2.

TABLE 1

Total cell number after each passage

| Passage Number | Cell Number of Control Group | Cell Number of Experimental Group |
| --- | --- | --- |
| 0 | 1.00E+07 | 1.00E+07 |
| 1 | 0.21E+07 | 0.51E+07 |
| 2 | 0.21E+07 | 0.81E+07 |
| 3 | 0.66E+07 | 1.67E+07 |
| 4 | 1.42E+07 | 7.96E+07 |
| 5 | 1.91E+07 | 2.05E+08 |
| 6 | 1.93E+07 | 6.18E+08 |
| 7 | 0.66E+07 | 1.58E+09 |
| 8 | — | 2.59E+09 |
| 9 | — | 3.01E+09 |
| 10 | — | 7.34E+09 |
| 11 | — | 1.64E+10 |
| 12 | — | 2.48E+10 |

In table 1 presents no further data available in the control group, due to the death of the cultured cells.

Figure 3:
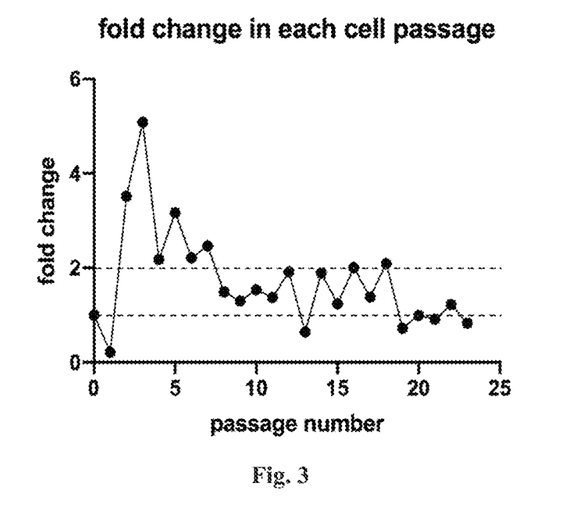
FIG. 3 is a graph of the fold change of total cell number in each cell passage in the long-term culture of human umbilical cord blood mononuclear cells in the experimental group. The fold change of total cell number per passage can be calculated by dividing the approximate number of cells harvested at the end of each passage by the approximate number of cells originally seeded into the culture at the beginning of this passage.
Figure 4:
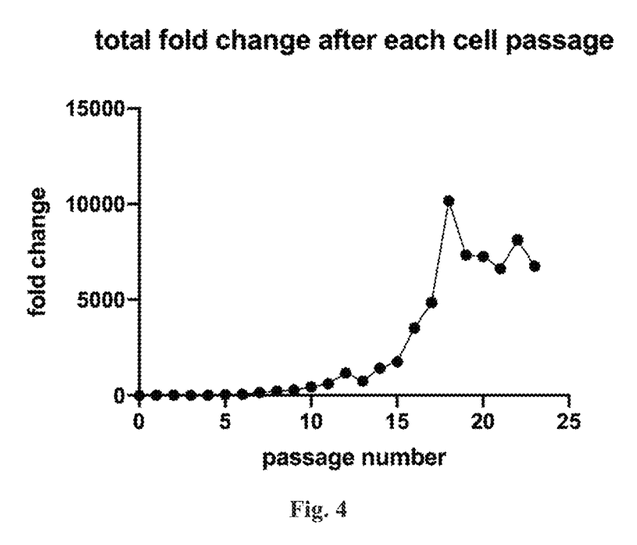
FIG. 4 is a graph of the total fold change of total cell number after each cell passage in the long-term culture of human umbilical cord blood mononuclear cells in the experimental group. The total fold change of total cell number after each passage can be calculated by dividing the approximate number of cells harvested at the end of this passage by the approximate number of cells originally seeded into the culture in passage 0.

The cell expansion can be maintained in experimental group up to 18 passages or more, then gradually stop growing (showed in FIG. 3 and FIG. 4). The cell number increased about $10^4$ folds at passage $18^{th}$ (showed in FIG. 4, cultured 72 days).

Therefore, a tankyrase inhibitor promotes a cell expansion and allows for the long-term expansion of cells derived from umbilical cord blood.

Example 2. Single Cell Sequencing Results of Cultured Cells

At passage $7^{th}$, single-cell RNA sequencing confirmed that 81.9% of total cells in the experimental group were erythroblast cells, 11.1% of total cells in the experimental group were human megakaryocyte-erythroid progenitor cells, and 2.3% of total cells in the experimental group were human common myeloid progenitor cells.

Figure 5:
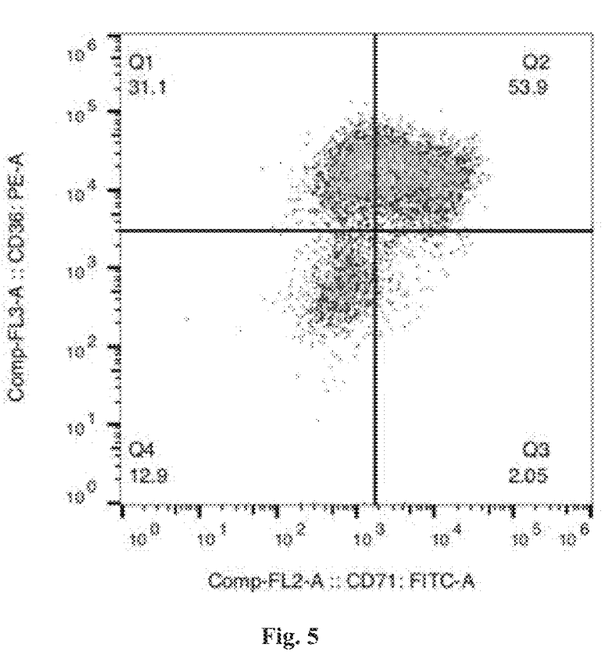
FIG. 5 is a graph of flow cytometer analysis of expanded cell population for CD36 and CD71 markers in the experimental group.

Example 3. Flow Cytometer Analysis Indicates that Most of Cells are Erythroblast Cell CD36 and CD71 are classical surface markers of the erythroblast cells. Flow cytometer analysis indicated that 85.0% of total cells were CD36 positive in the experimental group, 55.95% of total cells were CD71 positive in the experimental group (showed in FIG. 5).

Example 4. The Cells can be Transduced with Ad35 Adenovirus with High Efficiency CD46 serves as a receptor for group B adenovirus, including Adenovirus serotype Ad35. Cells with CD46 expression can be transduced with Ad35 adenovirus with high efficiency.

To determine whether the cells in the culture are CD46 positive, the cells in the expanded population of passage $8^{th}$ were stained with anti-CD46-PE. Flow cytometer analysis of the cells showed that 98.8% of these cells were CD46 positive, indicating that these cells could be transduced with Ad35 adenovirus with high efficiency.

To determine whether the human megakaryocyte-erythroid progenitor, or the human common myeloid progenitor in the culture are CD46 positive, the CD36 and CD71 double negative cells in the expanded population of passage $8^{th}$ were FACS sorted and then stained with anti-CD46-PE. Flow cytometer analysis of the sorted CD36 and CD71 double negative cells showed that 96.6% of these cells were CD46 positive. This result suggested that the human megakaryocyte-erythroid progenitors or the human common myeloid progenitors were CD46 positive and could be transduced with Ad35 adenovirus with high efficiency.

Figure 6:
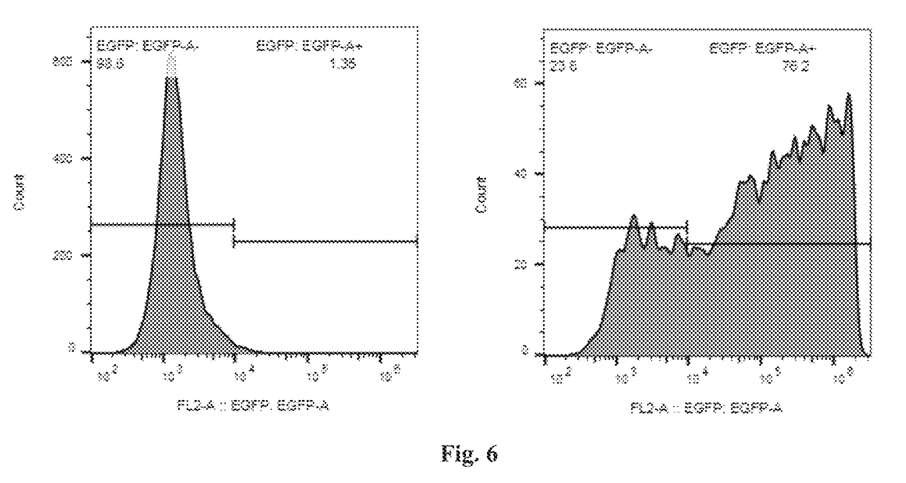
FIG. 6 is graphs of flow cytometer analysis of expanded cell population for EGFP before (left) and after (right) the Ad35-EGFP recombinant adenovirus transduction. 72h after transduction, 76.2% of cells were GFP positive.

The cells of passage $8^{th}$ were transduced with Ad35-EGFP recombinant adenovirus. 72h after transduction, 76.2% of cells were GFP positive and the multiplicity of infection (MOI) was 1000 (showed in FIG. 6). These results suggested that these cells were susceptible to Ad35-mediated gene manipulation.

Figure 7:
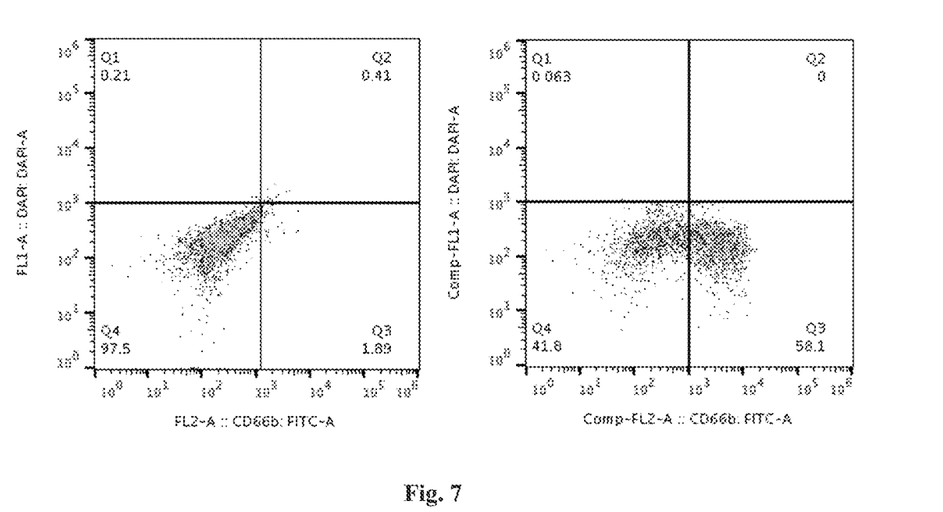
FIG. 7 is graphs of flow cytometer analysis of expanded cell population for CD66b before (left) and after (right) the differentiation.

Example 5. Flow Cytometer Analysis Shows the Cells have the Capacity to Differentiate into Neutrophils and Monocytes Human umbilical cord blood mononuclear cells were cultured in E6 medium supplemented with 3i+X composition (the same as that in EXAMPLE 1) to passage $5^{th}$, then switched to differentiation medium comprising: RPMI1640 culture medium, 10% FBS and 20 ng/ml of GCSF. 3 days later, cells were collected and subjected to flow cytometer analysis for CD66b expression. CD66b is a classical surface marker of the human neutrophil. 58.1% of cells were CD66b positive when treated with GCSF for 3 days, demonstrated by flow cytometer analysis (showed in FIG. 7).

Figure 8:
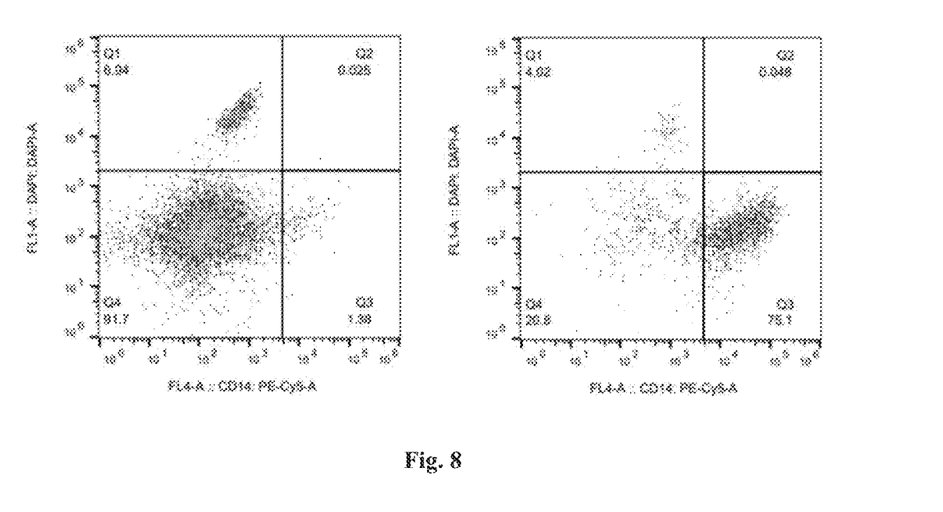
FIG. 8 is graphs of flow cytometer analysis of expanded cell population for CD14 before (left) and after (right) the differentiation.

Human umbilical cord blood mononuclear cells were cultured in E6 medium supplemented with 3i+X composition (the same as that in EXAMPLE 1) to passage $5^{th}$, then switched to differentiation medium comprising: RPMI1640 culture medium, 10% FBS and 20 ng/ml of GM-CSF for 8 days differentiation. Then, the cells were collected and the flow cytometer analysis was carried out to measure the expression of CD14. CD14 is a classical surface marker of the human monocyte. 75.1% of cells were CD14 positive when treated with GM-CSF for 7 days, demonstrate by flow cytometer analysis (showed in FIG. 8).

Example 6. Different Tankyrase Inhibitors can Promote Cell Expansion $2 \times 10^6$ of human umbilical cord blood mononuclear cells were cultured in E6 medium supplemented with 3i composition (the same as that in EXAMPLE 1) as a control group; and $2 \times 10^6$ of human umbilical cord blood mononuclear cells were cultured in E6 medium supplemented with 3i+X composition (the same as that in EXAMPLE 1) as experimental groups, wherein X presented the tankyrase inhibitor, and different tankyrase inhibitors were selected from JW55, RK-287107, WIKI4, XAV939 or TC-E5001 in different experimental groups.

Figure 9A:
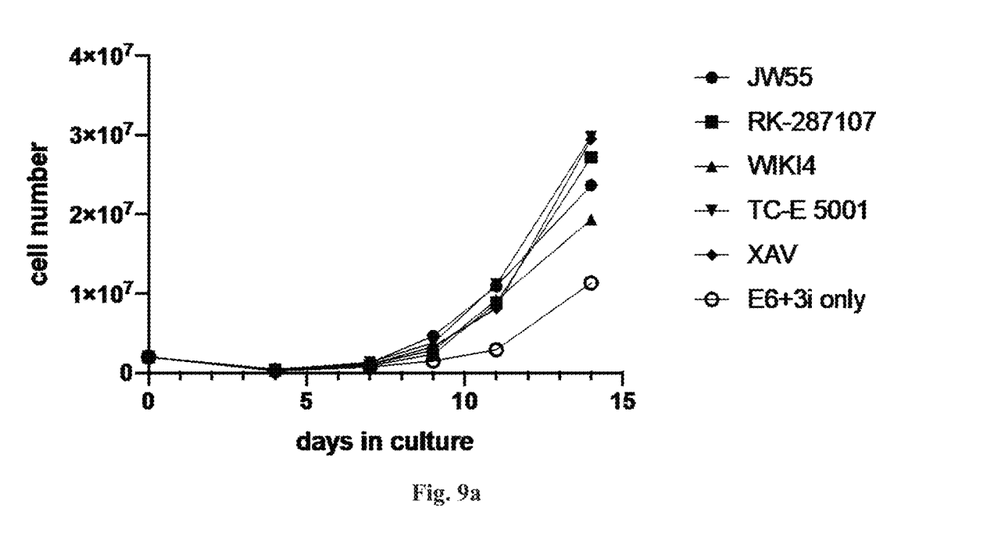
FIG. 9a is a graph of the total cell numbers of different experimental groups cultured in E6 medium with different tankyrase inhibitors at different time point in the culture of human umbilical cord blood mononuclear cells.
Figure 9B:
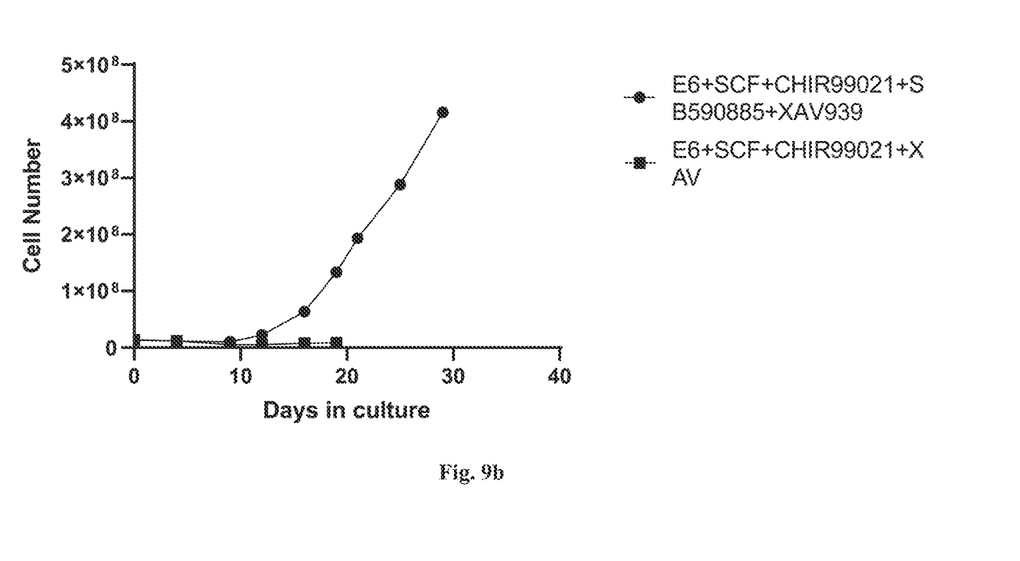
FIGS. 9b and 9c are the graphs of the total cell numbers of different experimental groups cultured in E6 medium with either remove SB590885 or CHIR99021 respectively at different time point in the culture of human umbilical cord blood mononuclear cells.
Figure 9C:
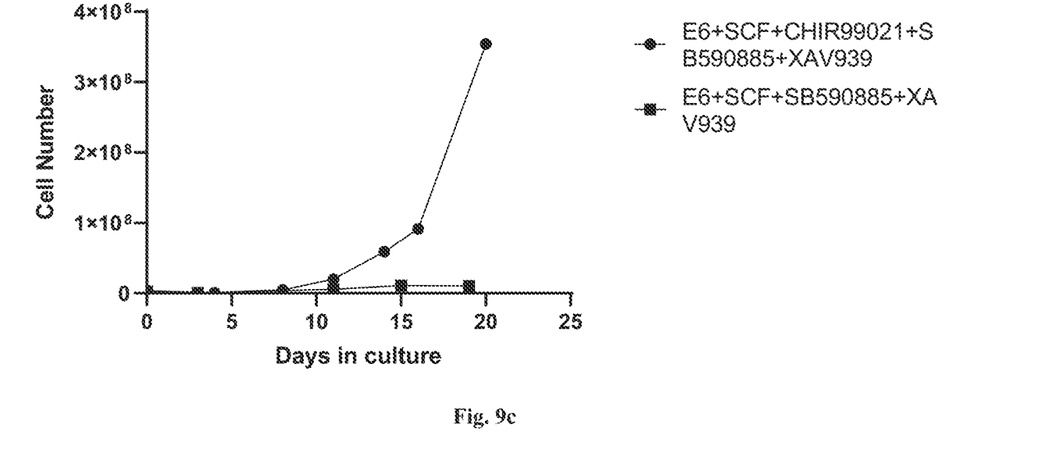
Figure 9D:
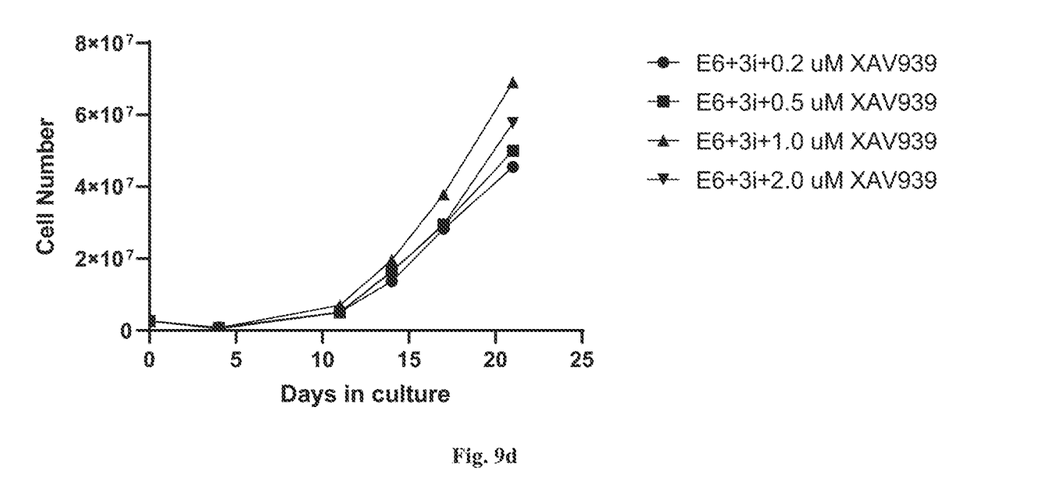
FIG. 9d is a graph of the total cell numbers of different experimental groups cultured in E6 medium with different concentrations of XAV939 at different time point in the culture of human umbilical cord blood mononuclear cells.
Figure 10:
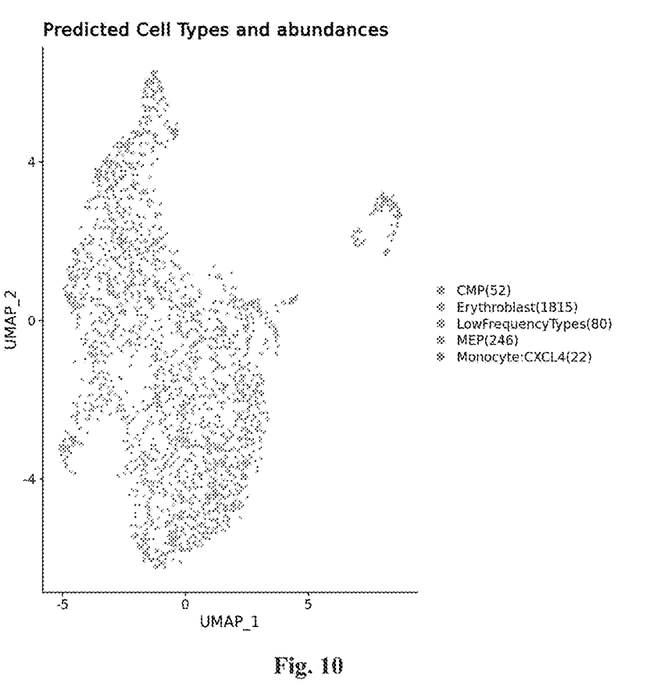
FIG. 10 is a graph of the single cell sequencing analysis of expanded cell population.

Expanded cell numbers of different experimental groups at passage $5^{th}$, day 14 are significantly greater than that of control group (showed in FIG. 9a). In addition, without either SB590885 (showed in FIG. 9b) or CHIR99021 (showed in FIG. 9c), the cells can maintain but the expanded cell numbers are significantly lower than that of 3i+X group. When concentration of XAV939 between 0.2 μM and 2 μM, the expanded cell numbers are about the same (showed in FIG. 9d).

Additionally, the inventors investigated effect of removal of SB590885, removal of CHIR99021, or experience of different concentrations of XAV939 on cell expansion. The cell counting results were shown in Tables 2, 3, and 4, respectively.

Thereof, different tankyrase inhibitors can promote cell expansion.

Thereof, tankyrase inhibitors together with both GSK-3 inhibitors and B-Raf kinase inhibitor can promote cell expansion.

The concentration of XAV939 at least between 0.2 μM and 2 μM can promote cell expansion.

TABLE 2

Total cell number of experience of removal of SB590885

| Days in culture | Cell Number of E6 + SCF + CHIR99021 + SB590885 + XAV939 | Cell Number of E6 + SCF + CHIR99021 + XAV |
|---|---|---|
| 0 | 1.35e+007 | 1.35e+007 |
| 4 | 1.13e+007 | 1.18e+007 |
| 9 | 1.04e+007 | 5210000 |
| 12 | 2.22e+007 | 5220000 |
| 16 | 6.36e+007 | 7830000 |
| 19 | 1.33e+008 | 8460000 |
| 21 | 1.93e+008 | — |
| 25 | 2.88e+008 | — |
| 29 | 4.16e+008 | — |

In table 2 presents no further data available in the E6+SCF+CHIR99021+XAV group, due to the death of the cultured cells.

TABLE 3

Total cell number of experience of removal of CHIR99021

| Days in culture | Cell Number of E6 + SCF + CHIR99021 + SB590885 + XAV939 | Cell Number of E6 + SCF + SB590885 + XAV939 |
|---|---|---|
| 0 | 3650000 | 3260000 |
| 3 | No data | 802000 |
| 4 | 1190000 | No data |
| 8 | 4860000 | No data |
| 11 | 2.02e+007 | 5770000 |
| 14 | 5.93e+007 | No data |
| 15 | No data | 1.12e+007 |
| 16 | 9.15e+007 | No data |
| 19 | No data | 1.05e+007 |
| 20 | 3.54e+008 | No data |

TABLE 4

Total cell number of experience of different concentrations of XAV939

| Days in culture | E6 + 3i + 0.2 uM XAV939 | E6 + 3i + 0.5 uM XAV939 | E6 + 3i + 1.0 uM XAV939 | E6 + 3i + 2.0 uM XAV939 |
|---|---|---|---|---|
| 0 | 2600000 | 2600000 | 2600000 | 2600000 |
| 4 | 854000 | 492000 | 789000 | 738000 |
| 11 | 5100000 | 5010000 | 7010000 | 5020000 |
| 14 | 1.37e+007 | 1.66e+007 | 1.96e+007 | 1.64e+007 |
| 17 | 2.83e+007 | 2.93e+007 | 3.79e+007 | 2.96e+007 |
| 21 | 4.55e+007 | 5e+007 | 6.91e+007 | 5.78e+007 |

Example 7. Cultured Cells can be Differentiated to Enucleated Erythrocyte

Figure 11:
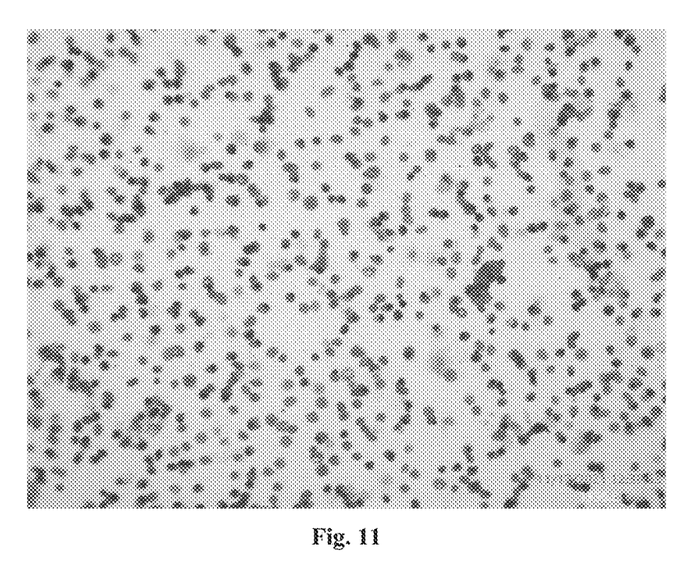
FIG. 11 is a picture of Benzidine and Giemsa staining of enucleated erythrocyte after 13 days of differentiation (200×).
Figure 12:
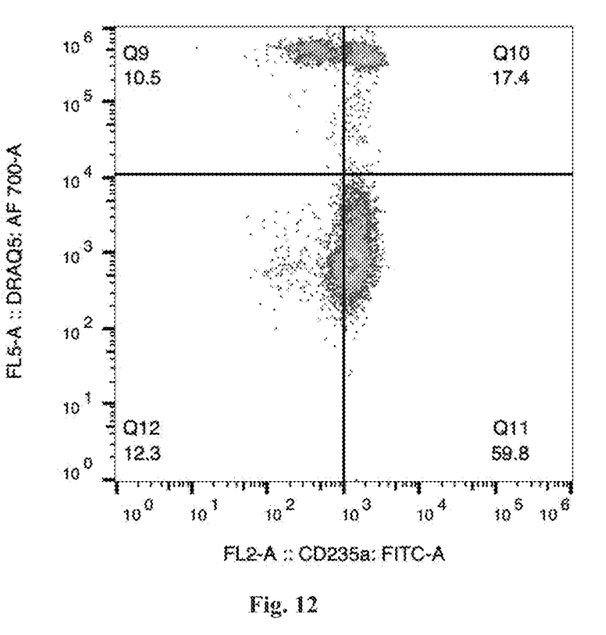
FIG. 12 is a graph of flow cytometer analysis of the erythroblast enucleation efficiency after 12 days of differentiation.

The cultured cells can be differentiated to enucleated red blood cells after 13 days of differentiation. Briefly, the mononuclear cells purified from umbilical cord blood were expanded in E6+3i+xav condition for 11 days; the cells were then cultured in differentiation medium which containing EPO+IL3+SCF for 7 days to expand the erythroblast cells. On day 8-10, the IL3 was removed from the medium; On day 11-12, the SCF was removed, the cell cultured in the medium with EPO only to enhance the enucleation of the erythroblast cells. On day 13, the enucleated erythrocytes were stained with Benzidine and Giemsa (showed in FIG. 11), as well as flow cytometry with CD235a and DRAQ5 (showed in FIG. 12). The percent of enucleated erythrocyte CD235a+ and DRAQ5− is about 60% of the population of cells.

What is claimed is:
1. A method for long-term ex vivo maintenance or expansion of one or more of a human erythroblast, a human megakaryocyte-erythroid progenitor, or a human common myeloid progenitor, comprising the step of:
   culturing the cells comprising one or more of the human erythroblast, the human megakaryocyte-erythroid progenitor, or the human common myeloid progenitor in a culture medium, wherein the culture medium comprises a combination of a tankyrase inhibitor, a growth factor, a B-Raf kinase inhibitor, and a GSK-3 inhibitor.

2. The method of claim 1, wherein the tankyrase inhibitor is one or more of XAV939, AZ-6102, JW-55, MN-64, TC-E 5001, WIKI4, RK-287107, MSC2504877, or G007-LK.

3. The method of claim 1, wherein the concentration of the tankyrase inhibitor in the culture medium is from 0.1 μM to 900 μM.

4. The method of claim 1, wherein the B-Raf kinase inhibitor is one or more of GDC-0879, PLX4032, GSK2118436, L-779450, DABRAFENIB, RAF709, BMS-908662, L-779450, LGX818, PLX3603, RAF265, RO5185426, vemurafenib, PLX8394, or SB590885.

5. The method of claim 1, wherein the GSK-3 inhibitor is one or more of CHIR99021, CHIR98014, LY2090314, ALSTERPAULLONE, BIO-ACETOXIME, AZD1080, 2-D08, SB216763, BIO, SB415286, TWS119, Tideglusib, A1070722, or AR -A014418.

6. The method of claim 1, wherein the growth factor is a stem cell factor (SCF).

7. The method of claim 6, wherein the concentration of the B-Raf kinase inhibitor in the culture medium is from 0.1 μM to 70 μM, the concentration of the tankyrase inhibitor in the culture medium is from 0.1 μM to 900 μM, the concentration of the GSK-3 inhibitor in the culture medium is from 0.1 μM to 70 μM, and the concentration of the stem cell factor in the culture medium is from 10 ng/ml to 100 ng/ml.

8. The method of claim 1, wherein a basal medium of the culture medium comprises: (1) DMEM/F12or IMDM, and (2) Neural Basal Medium.

9. The method of claim 8, wherein the DMEM/F12 and the Neural Basal Medium in the culture medium are in a ratio of 5:1 to 1:5.

10. The method of claim 1, wherein
the tankyrase inhibitor is XAV939,
the B-Raf kinase inhibitor is SB590885,
the GSK-3 inhibitor is CHIR99021, and
the growth factor is stem cell factor.

11. The method of claim 10, wherein
the concentration of XAV939 in the culture medium is 0.1 μM-20 μM,
the concentration of SB590885 in the culture medium is not more than 5 μM,
the concentration of CHIR99021 in the culture medium is not more than 10 μM, and
the concentration of the stem cell factor in the culture medium is 10 ng/ml to 100 ng/ml.

12. The method of claim 1, wherein the culture medium further comprises one or more supplements of insulin, transferrin, HSA, putrescine, progesterone, or linolenic acid.

13. The method of claim 11, wherein the culture medium is supplemented with insulin, transferrin, HSA, putrescine, progesterone, and linolenic acid.

14. The method of claim 1, wherein the human erythroblast, the human megakaryocyte-erythroid progenitor, or the human common myeloid progenitor cell is derived from an umbilical cord blood mononuclear cell, a hematopoietic stem cell, an embryonic stem cell, an induced pluripotent stem cell or a non-embryonic (adult) stem cell.

15. The method of claim 1, wherein any of the human erythroblast, the human megakaryocyte-erythroid progenitor, or the human common myeloid progenitor is capable to expand long term in the ex vivo culture medium, and the obtained cells after expansion remain morphologically unchanged and have the capacity to differentiate, wherein the obtained cells after expansion are $CD46^+$.

* * * * *